(12) United States Patent
Van Citters et al.

(10) Patent No.: US 10,448,958 B2
(45) Date of Patent: Oct. 22, 2019

(54) METHOD OF ENHANCING INTERDIGITATION OF BONE CEMENT TO BONE FOR ATTACHMENT OF PROSTHESIS TO BONE DURING ARTHROPLASTY

(71) Applicant: THE TRUSTEES OF DARTMOUTH COLLEGE, Hanover, NH (US)

(72) Inventors: Douglas W. Van Citters, Hanover, NH (US); Bridget E. Shaia, Richmond, VA (US); Spencer H. Amundsen, Lebanon, NH (US); James A. Yang, Palatine, IL (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 373 days.

(21) Appl. No.: 15/189,858

(22) Filed: Jun. 22, 2016

(65) Prior Publication Data

US 2016/0374693 A1    Dec. 29, 2016

Related U.S. Application Data

(60) Provisional application No. 62/183,393, filed on Jun. 23, 2015.

(51) Int. Cl.
*A61B 17/16* (2006.01)
*A61B 17/17* (2006.01)
(Continued)

(52) U.S. Cl.
CPC ...... *A61B 17/1604* (2013.01); *A61B 17/1666* (2013.01); *A61B 17/1684* (2013.01);
(Continued)

(58) Field of Classification Search
CPC ............................ A61B 17/1604; A61B 2/389
See application file for complete search history.

(56) References Cited

U.S. PATENT DOCUMENTS

| | | | | |
|---|---|---|---|---|
| 5,282,866 A | * | 2/1994 | Cohen | A61B 17/1604 623/20.34 |
| 2005/0143745 A1 | * | 6/2005 | Hodorek | A61B 17/157 606/87 |
| 2013/0144350 A1 | * | 6/2013 | Yoko | A61B 17/1764 606/86 R |

OTHER PUBLICATIONS

Abu-Amer, et al. (2007). "Aseptic Loosening of Total Joint Replacements: Mechanisms Underlying Osteolysis and Potential Therapies." Arthritis Research & Therapy. 9. Suppl 1: S6.

(Continued)

*Primary Examiner* — Olivia C Chang
(74) *Attorney, Agent, or Firm* — Lathrop Gage LLP (57) ABSTRACT

A method of attaching prosthetic implants to bone, applicable to tibia, patella, acetabulum, glenoid, or femur, includes trimming an articular surface of the bone, leaving a trimmed surface. Holes are punched or drilled into the surface in a predetermined array before polymethyl methacrylate bone cement is used to attach the surface to the implant. In an embodiment, the holes are punched by placing a punch-plate with sharpened punch spikes on the surface, and striking the punch plate to drive punches into the trimmed surface. In another embodiment, holes are drilled using a drilling template with predrilled guidance holes placed on the surface of the bone. In another embodiment, holes are drilled by positioning a robotic drill over the trimmed surface; adjusting a drilling pattern of the robotic drill according to the trimmed surface; and using the robotic drill to drill holes of predetermined depth according to the drilling pattern.

7 Claims, 8 Drawing Sheets

(51) Int. Cl.
A61F 2/38 (2006.01)
A61F 2/46 (2006.01)
A61B 34/30 (2016.01)
A61B 17/20 (2006.01)
A61F 2/30 (2006.01)

(52) U.S. Cl.
CPC ........ *A61B 17/1746* (2013.01); *A61F 2/3877* (2013.01); *A61F 2/4684* (2013.01); *A61B 17/1675* (2013.01); *A61B 17/1677* (2013.01); *A61B 17/1764* (2013.01); *A61B 17/1767* (2013.01); *A61B 17/1778* (2016.11); *A61B 17/205* (2013.01); *A61B 34/30* (2016.02); *A61F 2/3859* (2013.01); *A61F 2002/30878* (2013.01); *A61F 2002/4631* (2013.01)

(56) References Cited

OTHER PUBLICATIONS

Ambrosio (2010). "Biomedical Composites." Boca Raton, FL: CRC, pp. 210-233.
Amundsen, et al. (Jul. 2014). "Proximal Tibia Perforation to Enhance Shear Strength at the Bone-Cement Interface." Proc. Of Pan Pacific Orthopaedic Congress, Hilton Waikoloa, Kona, Hawaii.
ASTM Standard D1621-10, 1959 (2010), "Standard Test Method for Compressive Properties of Rigid Cellular Plastics," ASTM International, West Conshohocken, PA, 2010, DOI: 10.1520/D1621-10.
ASTM Standard F1839-08, 1997 (2012), "Standard Specification for Rigid Polyurethane Foam for Use as a Standard Material for Testing Orthopaedic Devices and Instruments," ASTM International, West Conshohocken, PA, 2012, DOI: 10.1520/F1839-08R12.
Author (Uknown) (2014). "Biomechanical Test Materials." Sawbones. Pacific Research Laboratories, Inc., 2014. Accessed at http://www.sawbones.com/UserFiles/Docs/biomechanical_catalog.pdf, Last accessed Mar. 15, 2017.
Author (Uknown). "Knee." in Orthopaedics and Sports Medicine. Dartmouth-Hitchcock. Accessed at http://www.dartmouthhitchcock.org/ortho/knee_pain_treatments.html. Last accessed on Apr. 20, 2017.
Author (Unkown). "Bone Cement: History, Performance, and Choice." DePuy Synthes. Accessed on Mar. 15, 2017.
Baleani, et al. (2003). "Fatigue Strength of PMMA Bone Cement Mixed with Gentamicin and Barium Sulphate vs. Pure PMMA." Proceedings of the Institution of Mechanical Engineers, Part H: Journal of Engineering in Medicine. 217, 1, pp. 9-12.
Black, et al. (1998). "Handbook of Biomaterial Properties." London: Chapman & Hall, pp. 506-507.
Blanton, et al. (1968). "Density of Fresh and Embalmed Human Compact and Cancellous Bone." American Journal of Physical Anthropology. 29, 1, pp. 39-44.
Boheme, et al. (2012). "Use of Polyurethane Foam in Orthopaedic Biomechanical Experimentation and Simulation." In "Polyurethane." InTech. Chapter 9, pp. 171-200.
Bozic, et al. (2009). "The Epidemiology of Revision Total Knee Arthroplasty in the United States." Clinical Orthopaedics and Related Research. 468, 1, pp. 45-51.
Brown (1984). "The Influence of Temperature and Specimen Size on the Flexural Properties of PMMA Bone Cement." Journal of Biomedical Materials Research. 18, 5, pp. 523-536.
Eveleigh (2001). "Principles of Bone Cement Mixing." British Journal of Perioperative Nursing, 11, 1, pp. 18-20.
Hamerman, et al. (1996). "Implications of Increased Bone Density in Osteoarthritis." Journal of Bone and Mineral Research. 11, 9, pp. 1205-1208.
Hamrock, et al. (1999). "Fundamentals of Machine Elements." Boston: WCB/McGraw-Hill. p. 242-245.
Helsen, et al. (2010). "Biomaterials: A Tantalus Experience." Heidelberg: Springer, pp. 46-47, 204-205 and 228-229.
Kurtz (2005). "Prevalence of Primary and Revision Total Hip and Knee Arthroplasty in the United States From 1990 Through 2002." The Journal of Bone and Joint Surgery. 87, 7, pp. 1487-1497.
Kurtz, et al. (2007). "Projections of Primary and Revision Hip and Knee Arthroplasty in the United States from 2005 to 2030." The Journal of Bone and Joint Surgery. 89, 4, pp. 780-785.
Lai, et al. (2013). "Chemical and Physical Properties of Bone Cement for Vertebroplasty." Biomedical Journal. 36, 4, pp. 162-167.
Lee, et al. (1978). "Some Clinically Relevant Variables Affecting the Mechanical Behaviour of Bone Cement." Archives of Orthopaedic and Traumatic Surgery. 92, 1, pp. 1-18.
Li, et al. (2013). "Subchondral Bone in Osteoarthritis: Insight into Risk Factors and Microstructural Changes." Arthritis Research & Therapy. 15, 6, p. 223.
Paul (2010). "Knee Replacement Implants." OrthoInfo. AAOS. Accessed at http://orthoinfo.aaos.org/topic.cfm?topic=a00221, Last access on Apr. 20, 2017.
Pbroks13 (2008). "Bone cross-section" Licensed under CCA 3.0 via Wikipedia. Accessed at https://en.wikipedia.org/wiki/File:Bone_cross-section.svg, last accessed on Mar. 15, 2017.
Ratner (2013) "Biomaterials Science: An Introduction to Materials in Medicine." Amsterdam: Elsevier Academic, pp. 892, 1484.
Roylance. (2001). "Transformation of Stresses and Strains." Massachusetts Institute of Technology, Cambridge, MA. May 14, 2001. MIT Open CourseWare. WeAccessed at < http://web.mit.edu/course/3/3.11/www/modules/trans.pdf >. Last accessed on Mar. 15, 2017.
Shakouri, et al. (Feb. 2014). "Experimental and Analytical Investigation of the Thermal Necrosis in High-speed Drilling of Bone." Journal of Engineering in Medicine. 228, 4, pp. 330-341.
Vilela (2011). "Osteoperosis." Neuroradiology. 53, 1, pp. 185-189.

* cited by examiner

Frontal    FIG. 11    Cross Sectional

METHOD OF ENHANCING INTERDIGITATION OF BONE CEMENT TO BONE FOR ATTACHMENT OF PROSTHESIS TO BONE DURING ARTHROPLASTY

CROSS-REFERENCE TO RELATED APPLICATIONS

The present application claims the benefit of priority to U.S. Provisional Patent Application No. 62/183,393 filed 23 Jun. 2015, the contents of which are incorporated herein by reference in its entirety.

FIELD

The present document relates to the field of arthroplasty—the surgical replacement of part of all of one or more joints of the human skeleton with implanted prosthetic replacements.

BACKGROUND

In the most common knee arthroplasty surgeries, the proximal end of the tibia and distal end of the femur are removed and replaced with metal and/or polymer prosthetics.

Long bones, including both the tibia and femur, include cortical bone and trabecular or cancellous bone. Cancellous bone is spongelike as it typically has form resembling a mesh, and is found primarily near ends of the bone, where its open-celled mesh supports cortical bone of the bearing surface at each joint. The mesh of cancellous bone is not empty, it is typically filled with soft tissue such as fat and marrow. Cortical bone is denser and more solid than cancellous bone, and not only forms a surface over cancellous bone but typically forms much of the long shaft portion of each long bone, as well as tendon and ligament attachment points and the bearing surfaces (articular surfaces) of each joint; typically the cortical bone bearing surfaces of the bones at each joint are separated by articular cartilage padding and lubricated with synovial fluid.

During arthroplasty of a joint involving long bones, some or all articular cartilage remaining in the joint is removed—indeed many arthroplasties are performed because of joint pain arising because the articular cartilage has been destroyed by injury or arthritis. Bone at the bearing surface of one or more bones of the joint is then trimmed back to make room for, and to fit onto, an implant that will functionally replace the bearing surface of that one or more bones. In the process of trimming back the bone, much cortical bone of the bearing surface, and some adjacent cortical bone, is removed, leaving residual bone, much residual bone at trimmed surfaces is newly exposed cancellous bone. Once bone trimming is completed, bone cement is used to attach the implant to the remaining bone, including to cancellous bone, of the long bone. The most common bone cement used in 2015 is based on polymethyl methacrylate (PMMA) with radiopaque filler and other additives.

In a total knee-replacement arthroplasty, implants cemented to that part of each bone remaining after bones are trimmed replace the articular surfaces of both femur and tibia, and in many such surgeries the articular surface of the patella.

Figure 1A:
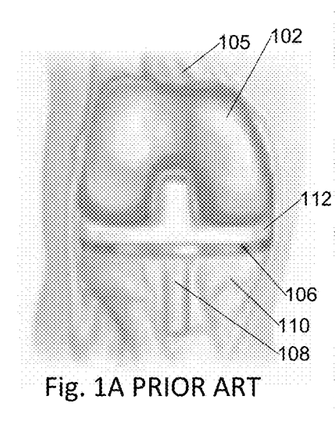
FIGS. 1A and 1B illustrate a PRIOR-ART total knee replacement as known in the art.
Figure 1B:
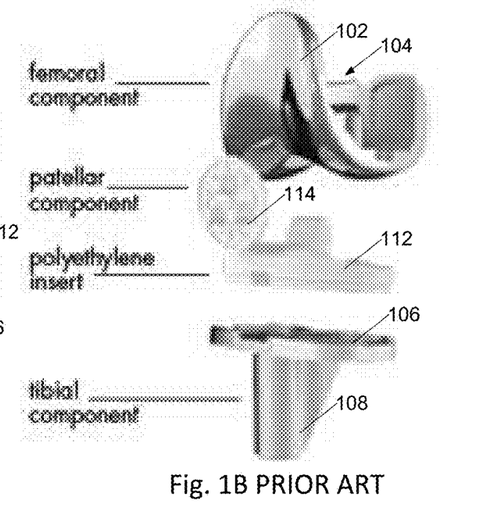

A typical prior-art total knee replacement arthroplasty may use implants as illustrated schematically in FIG. 1A as assembled into a patient, and in FIG. 1B as an exploded diagram showing each individual implant. A first implant 102, or femoral component, is formed with a socket 104 that attaches to residual bone of femur 105. A second implant 106, or tibial component, is formed with a stabilizing protrusion 108 that is configured to extend distally from the joint into a slot trimmed into residual tibia 110. A plastic insert 112 disposed between the first 102 and second 104 implants serves to pad and lubricate the joint and keep the first and second implants from abrading each other. A third implant 114, or patellar component, may in some cases be affixed to the underside of the patella (not shown), where it slides on first implant 102 as the knee bends.

SUMMARY

In an embodiment, a method of attaching a prosthetic implant to a tibia includes trimming away an articular surface of the tibia, leaving a trimmed surface. Holes are punched into the surface by placing a punch-plate with sharpened punches on the trimmed surface, and striking the punch plate to drive the punches into the trimmed surface. The punch plate is removed and polymethyl methacrylate bone cement is used to attach the trimmed surface to a prosthetic implant.

In another embodiment, a method of attaching a prosthetic implant to a tibia includes using a drilling template having a plurality of predrilled guidance holes placed on the trimmed surface of the tibia, and a hand drill to drill holes of predetermined depth through the guidance holes of the template.

In another embodiment, a method of attaching a prosthetic implant to a tibia includes trimming away an articular surface of the tibia, leaving a trimmed surface; positioning a robotic drilling system over the trimmed surface of the tibia; adjusting a drilling pattern of the robotic drilling system according to the trimmed surface of the tibia; using the robotic drilling system to drill holes of predetermined depth according to the drilling pattern into the trimmed surface of the tibia; and using a polymethyl methacrylate bone cement to attach the trimmed surface to a prosthetic implant.

DETAILED DESCRIPTION OF THE EMBODIMENTS

It is desirable that each implant of an arthroplasty, including a total knee arthroplasty (TKA), remain well attached to the bone whose articular surface it replaces and to which it was attached during surgery. Whenever an implant becomes loosened from the bone, remaining bone may degrade through osteolysis, and the patient may suffer pain and instability that interfere with mobility; it may become necessary to remove and replace the implant to restore patient mobility. Removal and replacement of implants is both an expensive and painful process that medical insurers, surgeons, and patients prefer to avoid.

It has been proposed that forming perforations in surfaces of trimmed residual bone, including particularly dense or sclerotic bone, adjacent to the implants, such as implants 102, 106, 114, will allow better attachment of bone cement to bone, and thereby decrease chances of implants becoming loosened from the residual bone. Some surgeons drill holes into the cut tibial surface in an effort to achieve better attachment of bone to implant, however hole patterns and spacing vary widely and effectiveness is unproven, particularly where some or all cortical bone has become extra-dense sclerotic bone. Sclerotic bone is known to interdigitate less effectively to existing bone cements than normal cortical bone, and is therefore more prone to failure with prior techniques.

We have experimented with perforators that create a predetermined and repeatable array of perforations of predetermined diameter, depth, and spacing. Among these tools are the experimental perforator tool of FIG. 2 and the improved, customized, tool of FIG. 3.

Figure 2:
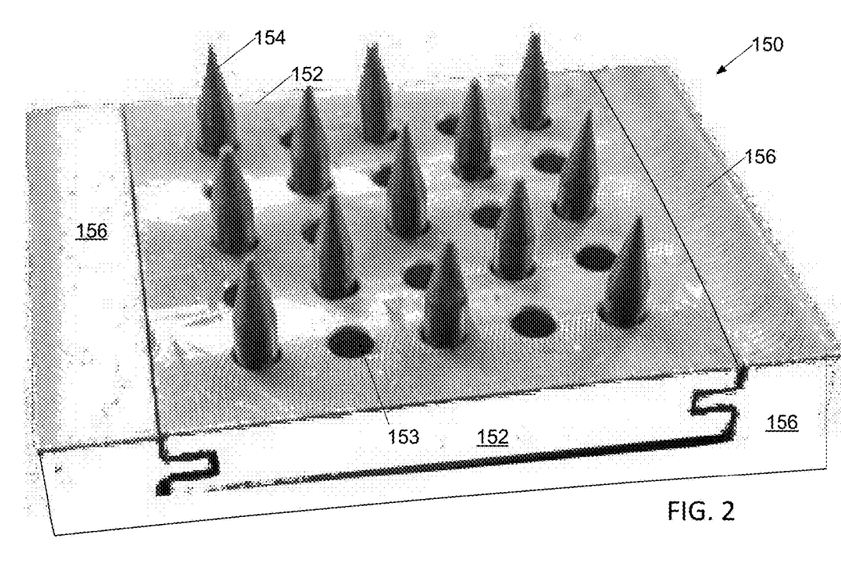
FIG. 2 illustrates an perforator tool.

The tool 150 of FIG. 2 has a sliding aluminum plate 152 with an array of holes 153 forming a grid pattern. Removable steel punch pins 154, each having a sharp point, are inserted into some or all of the holes, and sliding plate 152 is then slid into an aluminum frame 156. Each pin has a maximum diameter of 3 mm and tapers to a point over a pin depth of 4.5 mm.

A mechanical model of bone is solid rigid polyurethane foam from Sawbones (Pacific Research Laboratories, Vashon, Wash.), as per ASTM Standard F-1839-08 in 40 PCF and 50 PCF foams for properties of a dense bone, such as cortical or sclerotic bone, and 20 PCF or less for cancellous bone.

EXPERIMENTS

Closed cell polyurethane foam of densities 10 PCF, 20 PCF, 30 PCF, and 40 PCF was obtained, and formed into blocks of the same dimensions, dimensions chosen to fit a clamp for placement into a shear-testing machine. These were tested with hole densities selected from zero holes/cm2, 1.0 holes/cm2, 1.5 holes/cm2 and 2.5 holes/cm2, the holes being punched into the foam by pressing the points of pins 154 of the tool of FIG. 2 into the foam blocks.

Titanium plates used to mimic the tibial tray of a TKA system had a 2 mm deep recessed square (33 mm×33 mm) to simulate the design of the tibial tray, with surface roughness similar to that found in clinical implants.

A medium viscosity PMMA bone cement, DePuy Smart-Set CMW (DePuy, Warsaw, Ind.) was used for this study in 15 gram portions placed on foam blocks 30 seconds after being mixed for 60 seconds, spread and worked into holes of foam and titanium plate over following 90-180 seconds, and clamped for 45 minutes to cure. Laboratory temperature was maintained between 20 and 22 C.

TABLE 1 peak shear load and failure modes versus foam and hole density

| Cement Batch | Foam Density (PCF) | Hole Density (holes/cm$^2$) | Peak at Failure (kN) | Failure Mode |
|---|---|---|---|---|
| 7 (CMW) | 20 | 1.0 | 3.341 | Block fracture |
| 7 (CMW) | 20 | 1.0 | 4.067 | Block fracture |
| 7 (CMW) | 20 | 1.0 | 3.988 | Block fracture |
| 7 (CMW) | 20 | 1.0 | 3.578 | Block fracture |
| 8 (CMW) | 10 | 0 | 1.26 | Bone-cement failure |
| 8 (CMW) | 10 | 0 | 1.929 | Bone-cement failure |
| 8 (CMW) | 40 | 0 | 2.969 | Bone-cement failure |
| 8 (CMW) | 40 | 0 | 4.897 | Bone-cement failure |
| 9 (CMW) | 10 | 1.0 | 1.168 | Bone-cement failure |
| 9 (CMW) | 20 | 0 | 2.387 | Bone-cement failure |
| 9 (CMW) | 30 | 1.0 | 4.974 | Block fracture |
| 9 (CMW) | 40 | 1.0 | 3.587 | Plate-cement failure |
| 10 (CMW) | 10 | 1.0 | 1.507 | Bone-cement failure |
| 10 (CMW) | 20 | 0 | 3.851 | Block fracture |
| 10 (CMW) | 30 | 1.0 | 5.071 | Block fracture |
| 10 (CMW) | 30 | 0 | 5.895 | Block fracture |
| 11 (CMW) | 10 | 0 | 0.9785 | Bone-cement failure |
| 11 (CMW) | 20 | 0 | 3.517 | Block fracture |
| 11 (CMW) | 30 | 0 | 4.878 | Block fracture |
| 11 (CMW) | 40 | 1.0 | 4.709 | Bone-cement failure |
| 12 (CMW) | 30 | 0 | 4.891 | Block fracture |
| 12 (CMW) | 30 | 1.0 | 5.796 | Block fracture |
| 12 (CMW) | 40 | 0 | 5.560 | Bone-cement failure |
| 12 (CMW) | 40 | 1.0 | 5.138 | Bone-cement failure |
| 13 (CMW) | 30 | 2.5 | 5.195 | Block fracture |
| 13 (CMW) | 40 | 1.5 | 4.821 | Bone-cement failure |
| 13 (CMW) | 40 | 1.5 | 4.25 | Bone-cement failure |
| 14 (CMW) | 30 | 2.5 | 5.549 | Block fracture |
| 14 (CMW) | 40 | 1.5 | 6.11 | Bone-cement failure |
| 14 (CMW) | 40 | 2.5 | 6.448 | Bone-cement failure |
| 14 (CMW) | 40 | 2.5 | 6.556 | Block fracture |
| 15 (CMW) | 30 | 2.5 | 5.009 | Block fracture |
| 15 (CMW) | 40 | 2.5 | 5.493 | Block fracture |
| 15 (CMW) | 40 | 2.5 | 5.385 | Block fracture |
| 16 (CMW) | 20 | 2.5 | 3.915 | Block fracture |
| 16 (CMW) | 20 | 2.5 | 4.066 | Block fracture |
| 16 (CMW) | 10 | 2.5 | 1.705 | Bone-cement failure |
| 16 (CMW) | 10 | 2.5 | 1.765 | Bone-cement failure |
| 17 (CMW) | 20 | 2.5 | 2.717 | Bone-cement failure |
| 17 (CMW) | 20 | 2.5 | 3.009 | Block fracture |

TABLE 1-continued peak shear load and failure modes versus foam and hole density

| Cement Batch | Foam Density (PCF) | Hole Density (holes/cm²) | Peak at Failure (kN) | Failure Mode |
|---|---|---|---|---|
| 17 (CMW) | 10 | 2.5 | 1.467 | Bone-cement failure |
| 17 (CMW) | 10 | 2.5 | 1.558 | Bone-cement failure |

It was found that perforation of 1 hole/cm2 was sufficient for foams of less than 30 PCF, but that perforation of 2.5 holes/cm² was more appropriate for foams of 40 PCF simulating cortical and sclerotic bone, while not degrading fixation of bone cement to cancellous bone.

TABLE 2

Hole Dimensions

| Hole Dimensions | Density/sq cm | Diameter mm | Depth mm |
|---|---|---|---|
| A | 0.6-6 (<50% area) | 1-5 | 2-5 |
| B | 2-6 (<50% area) | 1-2 | 2-5 |
| C | 1-6 (<50% area) | 1-4 | 2-5 |
| D | 2.5 | 3 | 4.5 |

We anticipate that best results may vary somewhat with types of bone found in each particular patient, and that areal hole density will be in the range of 0.5 to 6 holes per square centimeter (Table 2), with hole diameter in the range of 1 to 5 mm, with hole depth 2 to 5 mm. We also anticipate that the hole density used on any particular patient is chosen such that the area of holes drilled in the tibial or other bone surface does not exceed 50% of the tibial surface, so that for hole diameters 1 to 2 mm, hole density is in the range of 2 to 6 per square cm; for hole diameters 2 to 3 mm, hole density is in the range of 1 to 6 per square cm; for hole diameters of 3 to 4 mm, hole density is in the range of 0.5 to 4 per square cm; and for hole diameters 4 to 5 mm, the hole density is in the range of 0.5 to 2.5 per square cm.

In a particular embodiment, hole density is 2.5/sq. cm, diameter is 3 mm, and depth 4.5 mm.

Surgical Tool and Procedure

Figure 3A:
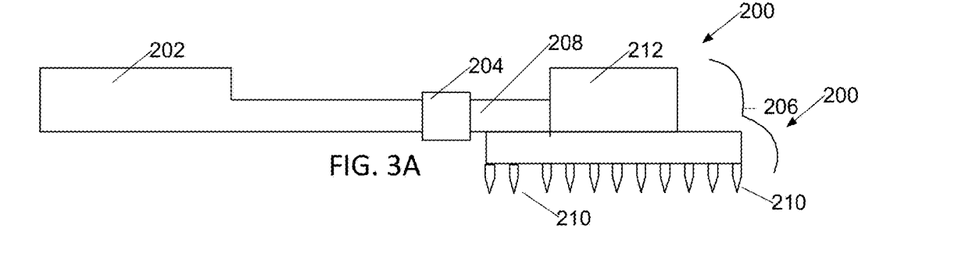
FIG. 3A illustrates a side view of an improved perforator tool tailored for use in knee arthroplasty.
Figure 3B:
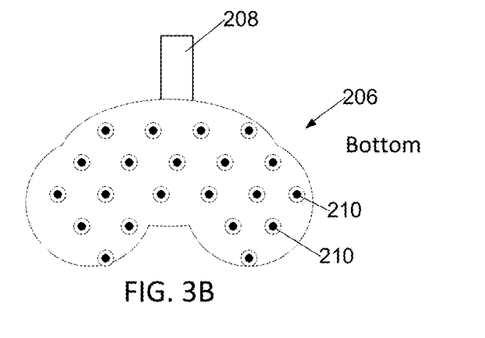
FIG. 3B illustrates a bottom view of a removable head of the tool of FIG. 3A showing the array of spikes.
Figure 3C:
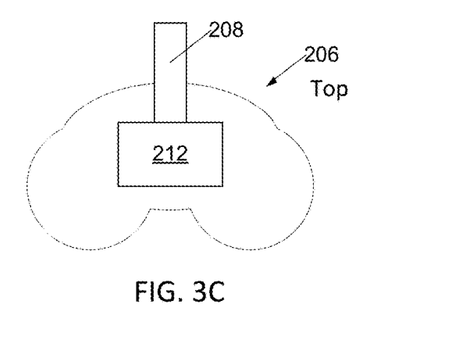
FIG. 3C is a top view of the removable head of FIG. 3B showing the striking plate.

It is therefore proposed that a tool as illustrated in FIGS. 3A, 3B, and 3C be used during knee arthroplasty surgeries. The tool 200 has a handle 202 fitted with a clamp 204 for attaching a coupling shaft 208 of a removable punch-plate 206. Removable punch-plate 206 is fabricated in several sizes, and provided in a kit with handle 202, so that a punch plate of size appropriate for the tibia of a particular patient can be selected and attached to handle 202 for use in a particular arthroplasty. In typical surgeries, the punch-plate selected is just small enough that all points 210 of the tool fit on bone of the trimmed surface of the tibia (not shown). The punch-plate of the tool also has a striking surface 212 adapted to being struck by a mallet.

Figure 4:
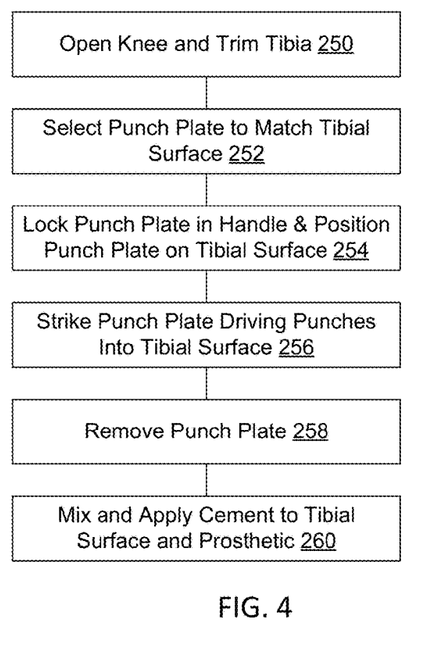
FIG. 4 is a flowchart of a method for performing arthroplasty that includes using the perforator.

During an arthroplasty, the patient is anaesthetized and arthroplasty surgery begins in traditional manner with trimming away 250 (FIG. 4) of the tibial articular surface and any remaining articular cartilage. A punch-plate 206 of appropriate size is then selected 252 such that all punches fit on the residual tibial surface, and attached 254 to handle 202, the punch plate is positioned on the tibial surface. The striking plate 212 of the punch plate 206 is then struck 256 with a mallet, driving the punch pins 210 into the trimmed tibial surface; punch plate 206 is then removed 258 with tool 200 from the surface. Surgery then continues with mixing and applying 260 of bone cement to both the tibial and prosthetic surfaces, being careful to work cement into holes of the tibia, and pressing the prosthetic implant onto the tibia.

In an embodiment the punch-plate has a punch density of 2-½ punches per square centimeter, each punch being 3 millimeters in diameter, and length of 4-½ millimeters.

Figure 5:
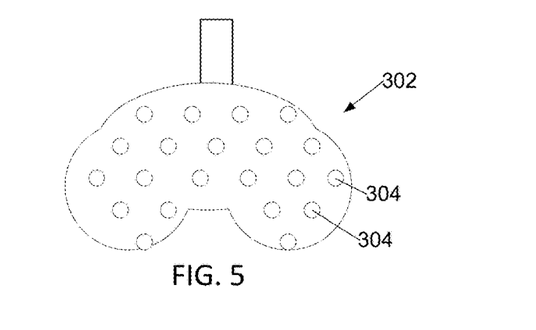
FIG. 5 is an illustration of an alternative template for perforating trimmed bone of a tibia, utilizing a hand drill.

In a alternative embodiment, as illustrated in FIG. 5, several drilling templates 302 having holes 304 are provided in a set of templates, each template being adapted attachment to the handle illustrated in FIG. 3A, and is used with a handheld drill using a bit with a depth indicating device. In use, after trimming bone of the tibia, the surgeon selects a template of appropriate size from the set of templates, attaches the template to the handle 202, and an assistant holds the template in position on the tibia while the surgeon uses the hand drill to drill through the template into the tibial surface. In this embodiment, a depth-gauge device may be attached to a bit rotated by the hand drill to limit hole depth to a predetermined depth.

Figure 6:
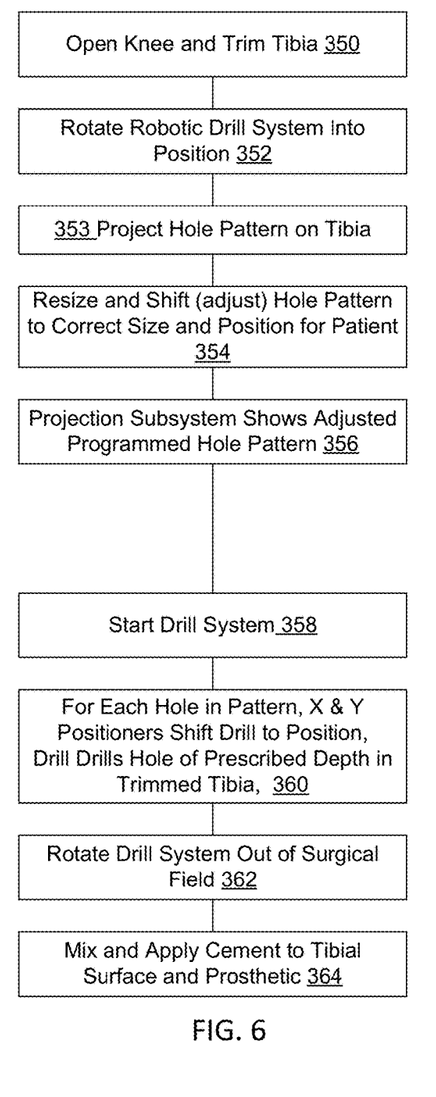
FIG. 6 is a flowchart of a method for performing arthroplasty that utilizes a robotic drill.
Figure 7:
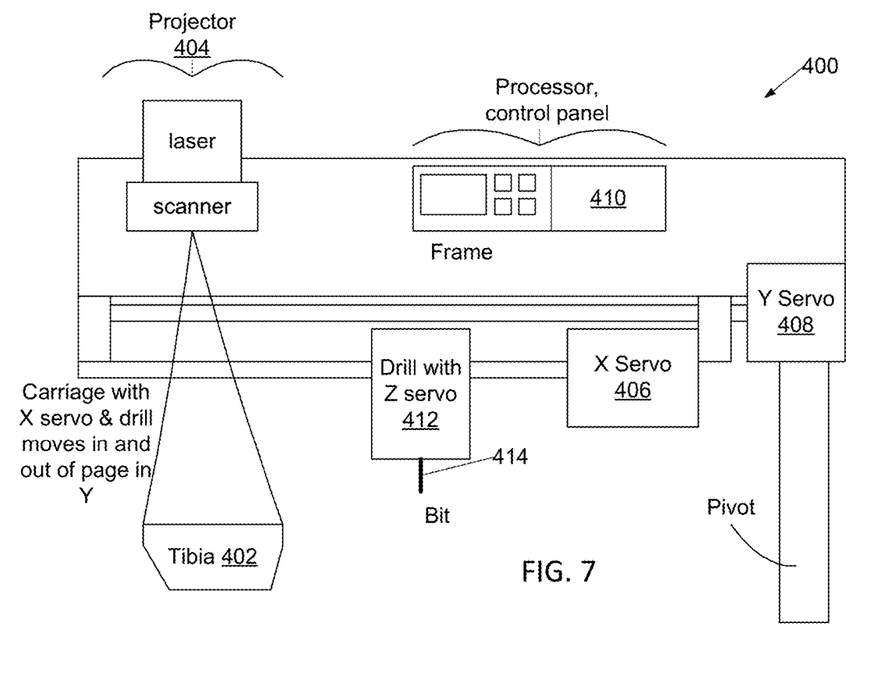
FIG. 7 is a sketch of an X-Y programmable robotic drilling apparatus usable in the method of FIG. 6.

FIG. 6 is a flowchart of an alternative method for performing arthroplasty that utilizes a robotic drill, the robotic drill may be of the type illustrated in FIG. 7 or, since polar coordinates are readily mapped to or from rectangular coordinates, may be one based on rotatable joints in articulated arms like the robotic surgical systems available from MAKO Surgical Corp, see below. In this method, after the tibia is trimmed 350, the surgeon or his assistant positions 352 a robotic drill unit 400 over the tibia 402 and uses a projector 404 of the robotic drill unit to project light 353 indicating locations of a particular programmed hole pattern on the tibia. The surgeon may then resize and relocate 354 the hole pattern so that all programmed hole locations are on the tibial surface; the adjusted hole pattern is projected 356 onto the tibial surface. Once satisfied with the hole pattern, the surgeon activates 358 the robotic drill unit. X 406 and Y 408 positioning servos of the robotic drill unit operate under control of processor 410 positions 360 a drilling head 412 of the drill unit over each hole location of the hole pattern, and the drilling head, which includes a vertical Z-axis servo, then drills a hole of predetermined depth using a drill bit or burr 414. When all holes are drilled, the robotic drill is shifted 362 out of the surgical field and the cement is mixed 364. We note that a robotic drill system provides the ability to drill holes of a particular preselected pattern, the pattern having a desired hole density and depth, far more quickly and with far greater precision of hole location and depth than possible with a hand drill even with drilling template 302. It is anticipated that the robotic drill may be equipped with a suction device to remove bone fragments severed from the tibia by a drill bit of the robotic drilling system.

Another alternative embodiment utilizes a robotic surgical system such as that offered by MAKO Surgical Corp., a division of Stryker Corporation. With this embodiment, prior to surgery, an X-ray computed tomography (CT) scan is performed to image the tibia. Cuts as necessary for trimming the tibial surface are planned using existing software, and an appropriate pattern of drill holes determined and incorporated into the planned cuts to the tibial surface. The resulting pattern of holes and trimming cuts is incorporated into a three dimensional computer model of the tibia.

In an embodiment, the Mako robotic surgical system supports its own weight, and the weight of a cutting tool, but the cutting tool is driven into the surface of the tibia by the surgeon. The surgical robotic system, however, resists the surgeon's movements whenever the surgeon attempts to cut bone beyond the planned cuts, serving effectively as an invisible drilling template.

In yet another alternative embodiment, the robotic surgical system actively moves the cutting tool to trim the surface of the tibia and drill the planned pattern of drill holes.

In addition to improving cementation of tibia to a prosthesis, we expect the method of trimming bone, perforating the trimmed surface of bone, and cementing prosthesis to bone will improve cementation of an articular surface prosthesis to a trimmed surface of patella in a total knee arthroplasty.

In the method 500 of performing an arthroplasty with both patella and tibial implants attached using perforations to improve adhesion of the cement (FIG. 8), the patient is anaesthetized and arthroplasty surgery begins in traditional manner with trimming away 502 (FIG. 4) of the tibial articular surface and any remaining articular cartilage. A punch-plate 206 of appropriate size is then selected 504 such that all punches fit on the residual tibial surface, and locked 506 to handle 202, the punch plate is positioned on the tibial surface. The striking plate 212 of the punch plate 206 is then struck 508 with a mallet, driving the punch pins 210 into the trimmed tibial surface; punch plate 206 is then removed with tool 200 from the surface.

Figure 8:
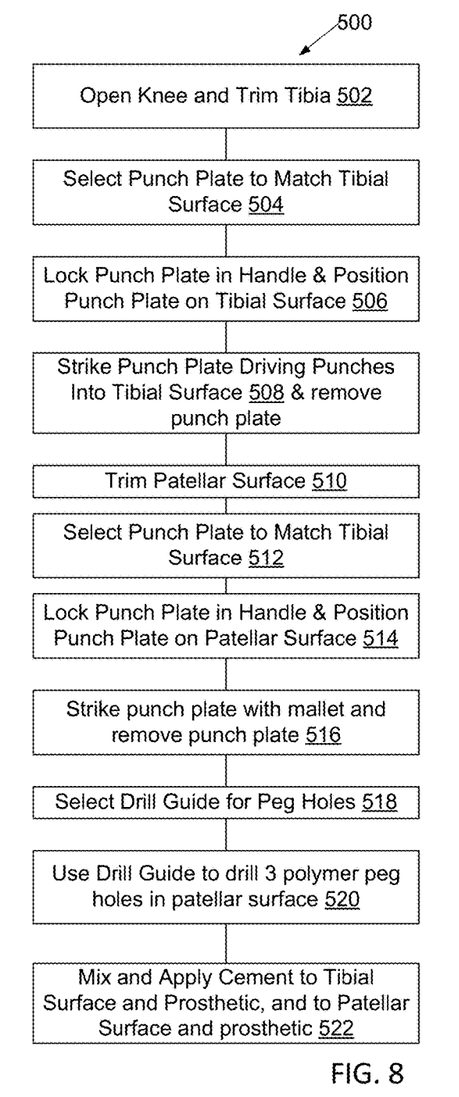
FIG. 8 is a flowchart of a knee arthroplasty that includes perforating both the tibia and patella with a punch.

The patella is then trimmed 510, typically leaving a flat trimmed surface and an appropriate-sized punch plate (not shown) is selected 514 and mated 512 with the trimmed surface of the patella. It is then struck 516 with the mallet to perforate the patellar surface.

Patellar prosthetics typically have a trio of pegs preventing their sliding on the patellar surface, so a drill guide is selected 518, positioned in a clamping device on the trimmed surface of the patella, and appropriate-sized holes drilled 520 to fit these pegs.

Surgery then continues with mixing and applying 522 of bone cement to both the tibial and prosthetic surfaces, being careful to work cement into holes of the tibia, and pressing the prosthetic implant onto the tibia; cement is also applied to the patellar and patellar prosthetic surfaces, worked into the holes, and the prosthetic patellar implant is pressed onto the patella such that its pegs fit into the peg holes.

Figure 9:
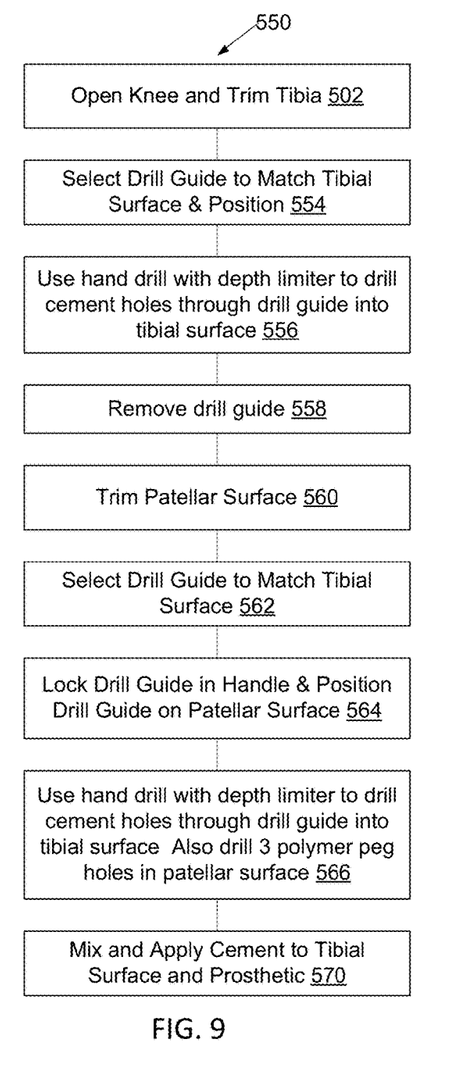
FIG. 9 is a flowchart of an alternative knee arthroplasty that includes perforating tibia and patella with a drill and drill guide to optimize cement attachment.

In an alternative embodiment 550, as illustrated in FIG. 9, using perforations to improve adhesion of the cement, the patient is anaesthetized and arthroplasty surgery begins in traditional manner with trimming away 502 of the tibial articular surface and any remaining articular cartilage. A drill-guide 302 of appropriate size is then selected 554 such that all holes fit on the residual tibial surface, and locked to handle 202, the drill guide is then positioned on the tibial surface. A portable electric drill equipped with a bit and a depth-limiting device on the bit is then used to drill 556 an array of holes on the tibial surface; the drill guide is then removed 558 from the surface.

The patella is trimmed 560, typically leaving a flat trimmed surface and an appropriate-sized drill-guide (not shown) selected 562, seated in a clamping device 564, and positioned on the trimmed surface of the patella. This drill guide may have holes of a first diameter to guide drilling perforation holes, and holes of a larger size to guide drilling of peg holes. A portable electric drill equipped with a bit and a depth-limiting device on the bit is then used to drill 566 an array of perforation holes, and another bit and depth-limiting device is used to drill peg holes, on the patellar surface; the drill guide is then removed from the surface.

Figure 10:
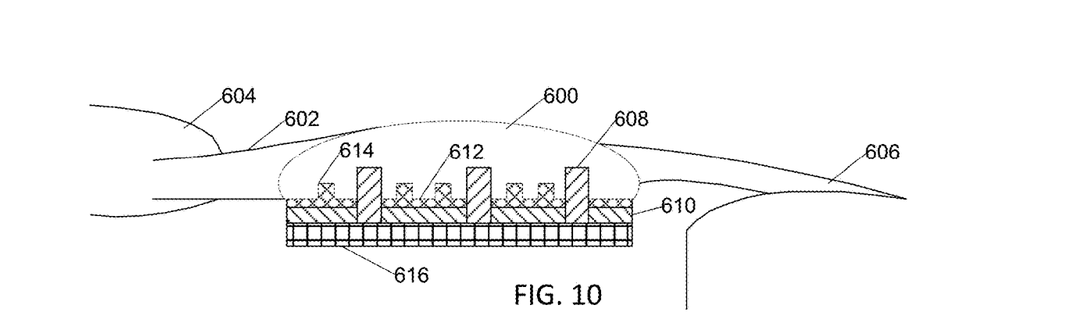
FIG. 10 is a cross sectional schematic drawing showing positioning pin holes and cement-bonding holes in a patella.

Surgery then continues with mixing and applying 570 of bone cement to both the tibial and prosthetic surfaces, being careful to work cement into holes of the tibia, and pressing the prosthetic implant onto the tibia; cement is also applied to the patellar and patellar prosthetic surfaces, worked into the holes, and the prosthetic patellar implant is pressed onto the patella such that its pegs fit into the peg holes. The resulting knee patellar arthroplasty resembles that illustrated in cross section in FIG. 10, where patella 600 is located in the patellar tendon 602 between quadriceps group muscles 604 and tibial insertion 606. Pegs 608 extend from prosthetic substrate 610 into holes in the patella 600. Cement 612 fills a narrow gap from patella to substrate 610, with cement extending into perforations 614, and a plastic bearing surface 616 is provided to interact with femoral and tibial surfaces of the joint.

Figure 11:
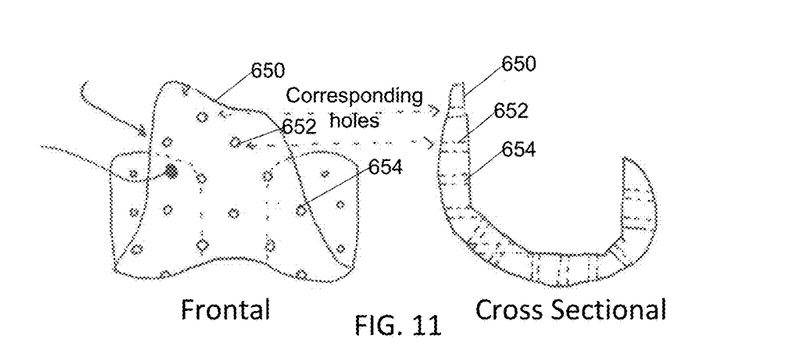
FIG. 11 is a frontal and cross sectional view of a dual-purpose fitting-trial piece and drill guide configured for perforating a trimmed end of a femur during a knee arthroplasty.

The femur at the knee joint is typically not flat. In embodiments, the knee arthroplasty may use a conventional femoral prosthetic, or, for additional security of bonding the prosthetic to the femur, perforations may be drilled with a combination fitting-trial piece/drill guide 650 as illustrated in FIG. 11 with frontal view on the left and cross sectional view on the right, with some corresponding holes illustrated. With this embodiment, after trimming the femur, and verification that the fitting-trial piece properly mates to the trimmed femoral surface, the fitting-trial piece/drill guide 650 is positioned on the trimmed femur and a portable drill, with appropriately-sized drill bit and depth control device, is used to drill through holes 652, 654 of the fitting-trial piece/drill guide 650 to prepare holes at the same depth, diameter, and areal density as previously discussed with reference to the tibia. The fitting-trial piece/drill guide 650 is then removed, cement is mixed and spread on both the trimmed surface of the femur and the prosthetic, and the prosthetic is pressed onto the prepared end of the femur (not shown).

It is anticipated that, while doing arthroplasty on knees that require implanted portions be cemented to more than one bone, a punch plate may be used to prepare one of the bones for the cement while the drill guide and hand drill may be used to prepare another bone of the same joint for the cement. It is also anticipated that some steps, such as drilling peg holes in the patella and punching perforation holes in the patella, can be done in reverse order to that described above. Similarly, cement may be mixed and applied separately to each bone-prosthetic seam, instead of with multiple seams at once as described with reference to patella and tibia (522, FIG. 8) above.

The method of improving cement-to-bone adhesion heretofore described with reference to knee arthroplasty is also applicable to hip and shoulder arthroplasty.

Figure 12A:
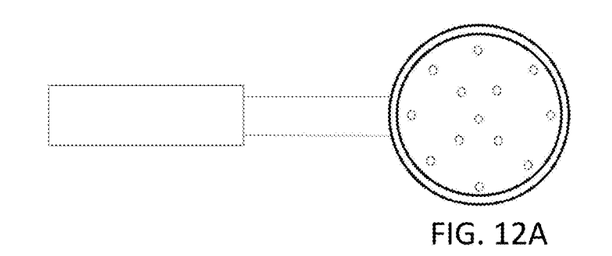
FIG. 12A is a top view illustration of a perforating punch or drill guide adapted for hip arthroplasty.
Figure 12B:
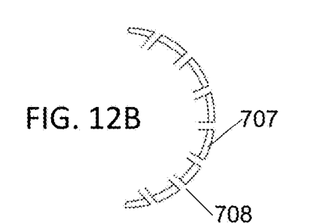
FIG. 12B is an illustration of a drill guide adapted for hip arthroplasty.
Figure 12C:
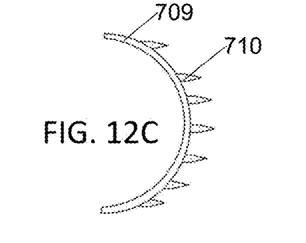
FIG. 12C is an illustration of a perforating punch adapted for hip arthroplasty.
Figure 13:
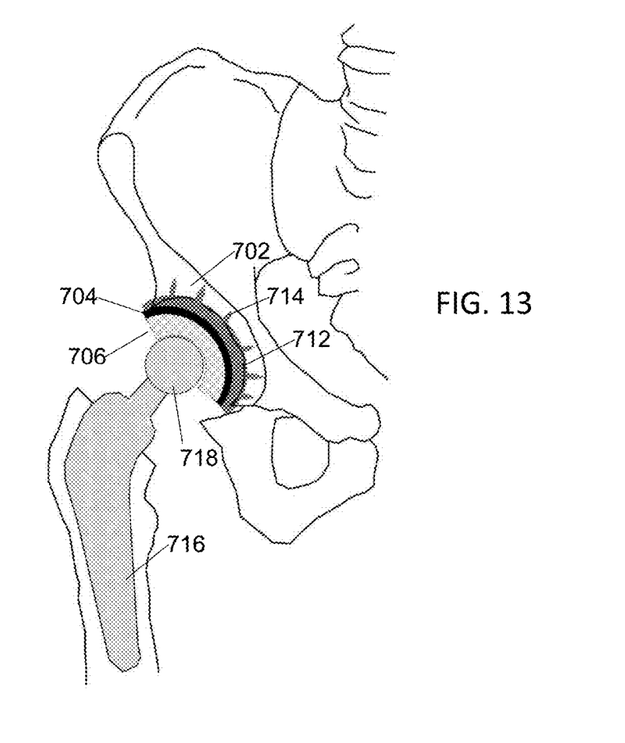
FIG. 13 is a cross sectional view of a hip arthroplasty performed according to the present invention.

A hip arthroplasty is performed by first trimming the acetabulum 702 (FIG. 13) to create a cavity into which an acetabular cup prosthetic socket 704 with polymer lining 706 will fit. In embodiments a drill guide 707 (FIG. 12B) or perforating punch 709 (FIG. 12A) adapted to fit in the cavity has holes 708 (FIG. 12B) or spikes 710 (FIG. 12C). In embodiments using the drill guide (707) the drill guide is placed in the cavity and a portable drill is used to prepare the cement holes having similar dimensions and spacing to those previously discussed with reference to the tibia. In embodiments using the perforating punch (709) the punch is placed in the cavity and whacked with a mallet to prepare the cement holes having similar dimensions and spacing to those previously discussed with reference to the tibia. Cement 712 (FIG. 13) is then applied between prosthetic socket 704 and acetabulum, entering into cement holes 714.

The femoral head is removed and femoral shaft is hollowed to fit a shaft of the femoral portion of the prosthetic.

Once the shaft is in place, the ball portion of the prosthetic is manipulated into the acetabular cup prosthetic.

Figure 14A:
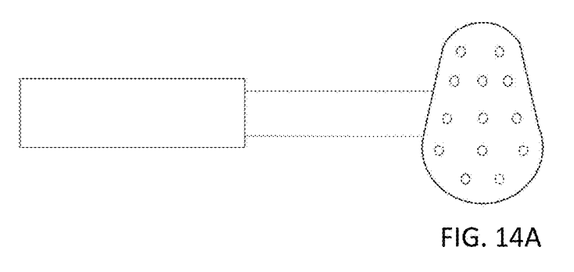
FIG. 14A is a top view illustration of a perforating punch or drill guide adapted for shoulder arthroplasty.
Figure 14B:
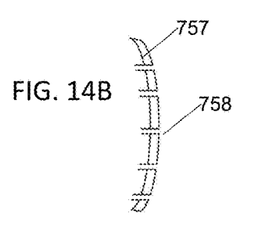
FIG. 14B is an illustration of a drill guide adapted for shoulder arthroplasty.
Figure 14C:
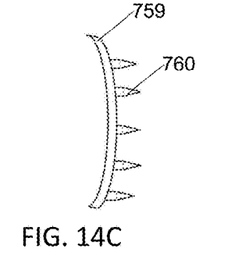
FIG. 14C is an illustration of a perforating punch adapted for shoulder arthroplasty.
Figure 15:
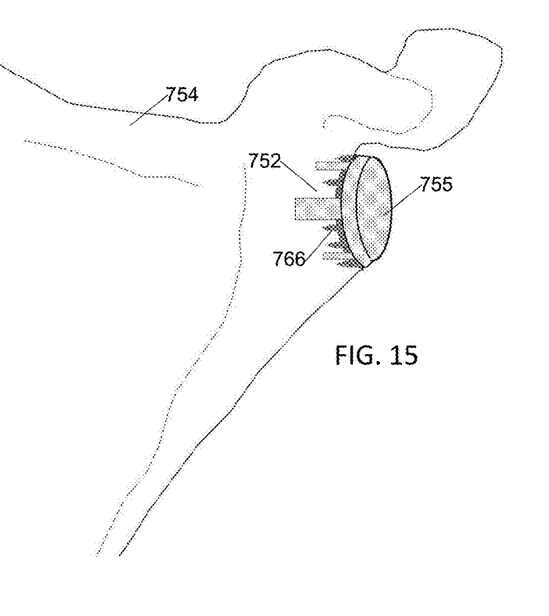
FIG. 15 is a perspective view of a shoulder arthroplasty performed according to the present invention.

A shoulder arthroplasty is performed by first trimming the glenoid fossa 752 of the scapula 754 (FIG. 15) to create a cavity into which a glenoid prosthetic 755 will fit. In embodiments a drill guide 757 or perforating punch 759 (FIG. 14A, 14B, 14C) adapted to fit in the cavity has holes 758 (FIG. 14B) or spikes 760 (FIG. 14C). In embodiments using the drill guide (757) the drill guide is placed in the cavity and a portable drill is used to prepare the cement holes having similar dimensions and spacing to those previously discussed with reference to the tibia. In embodiments using the perforating punch (759) the punch is placed in the cavity and whacked with a mallet to prepare the cement holes having similar dimensions and spacing to those previously discussed with reference to the tibia. Cement is then applied between prosthetic 755 and scapula, entering into cement holes 766.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of attaching a prosthetic implant to a bone comprising:
   trimming away an articular surface of the bone, leaving a trimmed surface;
   placing a punch-plate having a plurality of distinct, parallel sharpened punches, the parallel sharpened punches perpendicular to and extending equally from a first surface of the punch-plate, the first surface being parallel to a strike surface of the punch-plate, on the trimmed surface of the bone, the plurality of sharpened punches in contact with the trimmed surface;
   using a mallet to strike a strike surface of the punch plate to drive the punches into the trimmed surface thereby forming an array of punched holes in the trimmed surface;
   removing the punch plate from the bone; and
   using a polymethyl methacrylate bone cement to attach the trimmed surface to the prosthetic implant, such that the polymethyl methacrylate bone cement penetrates into the punched holes.

2. The method of claim 1, wherein the punch-plate has a punch density of approximately 2-½ punches per square centimeter, each punch being approximately 3 millimeters in diameter, and having a length of approximately 4-½ millimeters.

3. The method of claim 1, wherein the bone is the articular surface of a tibia at a knee.

4. The method of claim 1, wherein the bone is the articular surface of a patella.

5. The method of claim 1, wherein the bone is the articular surface of a femur at a knee.

6. The method of claim 1, wherein the hole density is between 1 and 6 per square centimeter, the hole depth is between two and five millimeters, the hole diameter is between one and four millimeters, and the total area of holes is less than one half the surface area of the bone.

7. The method of claim 3 wherein the hole density is between 1 and 6 per square centimeter, the hole depth is between two and five millimeters, the hole diameter is between one and four millimeters, and the total area of holes is less than one half the surface area of the bone.

* * * * *